United States Patent [19]

Proni et al.

[11] Patent Number: 4,957,008
[45] Date of Patent: Sep. 18, 1990

[54] FLUID SAMPLING AND TRANSFER VALVE ASSEMBLY

[75] Inventors: Oscar Proni; Ervin Fayer, both of Hollywood; George G. Dominick, Miramar, all of Fla.

[73] Assignee: Coulter Electronics, Inc., Hialeah, Fla.

[21] Appl. No.: 290,963

[22] Filed: Dec. 28, 1988

[51] Int. Cl.⁵ .............................................. G01N 1/10
[52] U.S. Cl. .............................. 73/864.83; 73/863.73; 436/179
[58] Field of Search ........... 73/864.83, 864.84, 863.73, 73/863.72, 863.71, 864.81, 864.82, 864.85, 864.86, 864.87; 436/179; 422/103

[56] References Cited

U.S. PATENT DOCUMENTS

| | | | |
|---|---|---|---|
| 2,656,508 | 10/1953 | Coulter et al. | 73/865.5 |
| 3,504,799 | 4/1970 | Ogle | 73/864.83 |
| 3,549,994 | 12/1970 | Rothermel et al. | 422/81 X |
| 3,567,390 | 3/1971 | Rothermel | 422/103 |
| 3,991,055 | 11/1976 | Godin et al. | 73/864.84 X |
| 4,152,391 | 5/1979 | Cabrera | 73/864.83 X |
| 4,445,391 | 5/1984 | Cabrera | 73/864.12 |
| 4,507,977 | 4/1985 | Cabrera | 73/864.12 |
| 4,702,889 | 10/1987 | Cabrera et al. | 73/863.73 |
| 4,726,932 | 2/1988 | Feier et al. | 73/863.73 X |
| 4,822,569 | 4/1989 | Pellegrino | 422/103 |
| 4,896,546 | 1/1990 | Cabrera et al. | 73/863.73 |

FOREIGN PATENT DOCUMENTS

| | | | |
|---|---|---|---|
| 816392 | 7/1969 | Canada | 73/864.83 |
| 249348 | 12/1987 | European Pat. Off. . | |
| 251741 | 11/1986 | Japan | 73/864.83 |

Primary Examiner—Tom Noland
Attorney, Agent, or Firm—Sidney N. Fox; Gerald R. Hibnick

[57] ABSTRACT

A liquid sampling, metering and transfer valve assembly for providing plural dilutions of a single liquid sample comprising a pair of outer stationary elements sandwiching a rotatable element, the rotatable element carrying precise volume segmenting passageways, the outer elements carrying counterpart passageways for communicating to the exterior of the valve assembly, one outer element carrying loops each for storing a precise volume of diluent and the other valve elements carrying through passageways for communicating to and from said respective loops. A continuous body of sample is introduced into the valve assembly along a path through a pair of the segmenting passageays and a pair of aliquot portions isolated from said parth. The rotatable element is operated to direct one aliquot along with the content of one loop to an exterior location for mixing. The other sample aliquot is retained. The thus formed mixture is reintroduced into the valve assembly along a path through the third segmenting passageway and an aliquot thereof is isolated. Both it and the retained sample aliquot then are directed from the valve assembly to respective testing locations along with the respective content of the remaining loops. Channels are provided in the inner faces of the outer elements and communicatively coupled, entry and outer ports enable cleaning reagent to be introduced therein, the sandwiched element being rotated 360 degrees whereby to rinse the facing interior surfaces of the valve assembly.

12 Claims, 5 Drawing Sheets

FLUID SAMPLING AND TRANSFER VALVE ASSEMBLY

CROSS-REFERENCE TO RELATED PATENTS AND PATENT APPLICATIONS

Reference is made to the following patents, each owned by the assignee of this application:
U.S. Pat. No. 3,549,994 granted Dec. 22, 1970
U.S. Pat. No. 3,567,390 granted Mar. 2, 1971
U.S. Pat. No. 4,152,391 granted May 1, 1979
U.S. Pat. No. 4,445,391 granted May 1, 1984
U.S. Pat. No. 4,507,977 granted Apr. 1, 1985
U.S. Pat. No. 4,702,889 granted Oct. 27, 1987

The disclosures of the above identified patents are hereby incorporated by reference herein for the purpose of providing background of the herein invention.

BACKGROUND OF THE INVENTION

This invention relates generally to liquid metering and transfer valves for use in a diluting system of the type wherein vessels, valves and connecting conduits are employed to measure, intermix, dilute and deliver fluids, particularly liquids, for the purpose of automatically making measurements and tests upon liquid samples for the medical, biological, chemical, industrial and allied fields.

In particular, the invention provides a multiposition fluid sampling, metering and delivery valve assembly operable with liquid and gaseous state fluids for delivering precise volumes of liquid samples and diluent respectively to pre-selected testing locations automatically without manual interaction and capable of being installed in a small, compact, stand-alone analyzer, said valve assembly capable of employing positive and/or negative pressure to move fluids therethrough in a reliable sequence, capable of performing the metering (measuring) of both sample and diluent within the valve assembly, said valve assembly further having means enabling self-cleaning and self-maintenance.

Apparatus of the general type with which the valve assembly of the herein invention is intended to operate employ the well known Coulter particle analyzing principle disclosed in U.S. Pat. No. 2,656,508 and are capable of many uses in the medical, biological, chemical and allied fields, in research as well as routine testing and requires means which can produce liquid mixtures of specific concentrations accurately and automatically. The analyzing apparatus is required to perform testing and measurements on a continuous basis with many tests made simultaneously and complex routines repeated with precision but with different samples. In such apparatus, the requisite liquid samples must be drawn and precisely measured, combined with preselected volumes of diluent to define the requisite dilutions and transferred to vessels within the apparatus for testing purposes. Often different degrees of dilution are required for determination of different parameters of the original sample. Sample quantities often are limited and hence the multiple operations and determinations preferably are performed utilizing a single liquid sample of relatively small volume and, accordingly, conservation of sample is a desired goal.

Accordingly, analytical apparatus of the type concerned are provided with diluting means incorporated as a part thereof for preparation and delivery to testing locations therewithin of sample suspensions of predetermined concentrations automatically and accurately, a major subsystem of said diluting means being a liquid metering and transfer valve assembly which includes internal segmenting passage means capable of being coupled to a source of liquid sample. A liquid sample is drawn along one path into said segmenting passage means and the valve assembly is operated to isolate a precise volume of said liquid sample from one internal path and place said precise volume into a second path. A desired volume of diluent is directed into the second path driving the measured precise volume of sample along with the diluent to deliver same to a testing vessel or station exterior of the valve assembly. Conventionally the source of said diluent is coupled to the valve assembly by suitable conduit means linked therebetween and driven by pump means and metering means provided within the apparatus.

Movement of the liquids is imparted by positive and/or negative pressure means effected by sources thereof coupled to the valve assembly and to said pump means and metering means. The apparatus includes myriad check valves and pinch valves required to control the flow of the various fluids within the apparatus. It would be desirable to provide a multifunctional metering and transfer valve assembly which would perform all measurement of the various liquids therewithin. The analyzing instrument desirably should be compact, highly reliable, modularly constructed at low cost particularly to provide for meeting the needs of physicians', veterinarians', clinical and alternative care testing requirements.

Preferably, the analyzing instrument should eliminate or at least minimize the interaction of the operator with the instrument, eliminating the necessity for manual dilutions, being capable of self-cleaning and self-maintaining, i.e. independent of the operator's intervention.

Thus, as mentioned, it becomes highly desirable to provide a sampling, metering and transfer valve assembly wherein all dilutions are provided by the valve assembly itself . . . all dilutions determined within the valve assembly, all volumetric metering of both sample and diluent effected within the valve assembly with means provided for backwashing and rinsing, including that of the coupling between the valve assembly and the sample source, that is, the aspirator probe through which the liquid sampled is drawn into the valve assembly. Thus a multiposition, multifunctional, stepwise programmably operable sampling, metering and transfer valve assembly which is capable of precise positioning on command, is desired.

Prior U.S. Pat. Nos., such as 3,567,390, 3,991,055, 4,152,391, 4,445,391, 4,507,977 and 4,702,889 provided examples of metering and transfer valve assemblies wherein internal measuring chambers, generally in the form of passageways, are provided.

The earliest of the above identified prior U.S. Pat. No. 3,567,390, provided a metering and transfer valve assembly having a pair of outer disc members and a central disc member sandwiched therebetween, its opposite surfaces frictionally engaged with the facing surface of the respective outer disc member. The discs are aligned axially and mounted on a spindle so that the outer discs are stationary while the center disc is rotatable between two positions. A pair of axially parallel segmenting passageway sets are provided in the central disc and matching passageways are provided so that in one position of the central disc, liquid sample is received within one segmenting passageway of one set. The central disc is rotated to a second position where a precise volume of the liquid sample is received within one segmenting passageway of one set. The central disc is rotated to a second position so as to subtend a precise volume of the liquid sample wihtin said one segmenting passageway and a known, externally metered volume of diluent is introduced into the valve assembly to sweep the subtended volume of liquid sample, along with said metered volume of diluent, to an exterior location for testing.

Simultaneous with the introduction of said liquid sample in the first position of the center valve disc, liquid is taken from said exterior location comprising a prior formed "first dilution" and transferred to one segmenting passageway of the second set. When the central disc is rotated to segment the precise volume of the liquid sample, the so-called "first dilution" also is segmented to provide a precise volume of the "first dilution" to form a "second dilution". Simultaneous with the delivery of the first mentioned dilution (liquid sample plus diluent) to said location exterior of the valve assembly, the segmented volume of the "first dilution" is swept from the one segmenting passageway of the second set along with a metered given volume of diluent to another exterior location where it constitutes a "second dilution". Note that the volumes of diluent are metered exterior of the valve assembly and delivered to the valve assembly. Additionally, the liquid sample is sequentially tested at said locations exterior of the valve assembly, the prior made "second dilution" being tested simultaneously with the testing of a current made "first dilution". However, the basic principle underlying the instant invention is set forth in said U.S. Pat. No. 3,567,390 with the two sets of segmenting passageways being formed in the center or rotatable disc of the valve assembly.

U.S. Pat. No. 4,152,391 provides for the forming of three dilutions employing a single metering and transfer valve assembly comprising a pair of stationary disc members and a center, rotatable disc member sandwiched there between. The center disc carries one set of axially parallel segmenting passageways. The structure also includes a pair of external measuring loops secured to the central disc and passing through slots formed in one of the outer, stationary discs. The loops carry a precise volume of liquid sample and one of which is filled alternatively with the other simultaneously with introduction of the liquid sample into the segmenting passageway of said one set. As with the structure disclosed in U.S. Pat. No. 3,567,390, diluent is metered exterior of the valve assembly and introduced to the valve assembly. The loops are arranged in parallel, so that only one is filled with the liquid sample at the time liquid sample is introduced into the one of the said set of segmenting passageways. However, that one loop is arranged in series with said one of said set of segmenting passageways to enable a single aspiration (or drawing step) to fill same simultaneously although two separate loading steps are required to fill both loops, alternatively. The said valve structure also included gallery formations defining paths for communicating with selected passageways. Further, slot means were required to be formed in one of the outer disc members in order to permit passage of the loops enabling rotation of the central disc so as to effect the semgentation.

U.S. Pat. No. 4,445,391 provided a liquid metering and transfer valve assembly wherein a measuring loop was secured to one of the stationary outer discs in addition to the set of axially parallel segmenting passageways formed in the center disc. A series path thus was defined through the valve assembly so that a single loading stop sufficed to fill both loop and one axial passageway of the segmenting passageway set and, with rotation of the central disc, and introduction of diluent, both the segmented precise volume of sample in the segmenting passageway and in the loop was delivered simultaneously to a pair of different testing locations along with given volumes of diluent, the latter being metered and stored exterior of the valve assembly. This structure was less expensive to manufacture since galleries and slots were not required. However, only a pair of dilutions could be made. The loop had only one function, that is, to measure a precise volume of liquid sample, the same liquid sample introduced into the segmenting passageway set.

U.S. Pat. No. 4,507,977 was generally similar in construction to that disclosed in U.S. Pat. No. 4,445,391 but for the provision of means to enable mounting of an additional probe (or aspirator) means for introducing an additional liquid into the valve assembly. While the two liquid samples were capable of being operated upon by a single valve assembly, the samples had to be taken successively and the loop remained only functional to measure a second volume of the same liquid sample simultaneously introduced to the segmenting passageway set.

Commonly with the prior valve assembly constructions described, metering of the diluent at locations exterior of the valve, involved the provision of plural metering units, pumps, pinch and check valves, resulting in complex arrangements and requiring much interior space, reducing the compactness of the analyzing system. Very simply put, it would be highly desirable to provide means whereby all liquids, including diluent, could be metered within the valve assembly yet without increasing the complexity of the valve assembly.

An improvement of significance was made to the general liquid metering and transfer valve art when U.S. Pat. No. 4,702,889 provided means for obviating a problem of leakage experienced at the junctions of the various interior passageways formed in the valve discs comprising the valve assemblies. Leakage was encountered from said junctions, material travelling as by capillarity, along the frictionally engaged facing surfaces of said valve discs to foul the circumferential surfaces of said valve assemblage. In particular, the structure of said valve assembly was improved by providing means defining a continuous channel in one of the frictionally engaged facing surfaces of at least one stationary disc and the facing surface of the center disc member frictionally engaged therewith. The channel was provided to extend along the periphery of said one surface and had an inlet and an outlet defining a path independent of any of the internal passageways within the valve assembly and non-interferent therewith. The continuous channel disclosed in the U.S. Pat. No. 4,702,889 comprised an outer groove formed in one of the frictionally engaged surfaces extending along the outer periphery of the face of the disc in which it is formed substantially the circumferential extent of said disc and continuing at a location near the inner periphery of said face as an inner groove extending substantially the extent of the central axis passageway of the disc, the grooves being concentric with the central axial passageway, whereby to intercept any eluded material escaping from any of the junctions of the said passageways and travelling along the engaged surfaces toward the inner and/or outer circumferential surfaces of the valve assembly, preventing the migration thereof to said circumferential surfaces. The thus defined "cleaning grooves" were bridged by a groove portion formed therebetween and connecting the pair of concentric grooves. Diluent or rinsing fluid, peferably liquid, was introduced to the "cleaning channel" thus defined via the inlet thereto. The rinse liquid passed through the channel to wash any residue from the channel, but did not serve to clean the engaged opposing faces of said discs. Where a groove was formed in one face of one of said frictionally engaged pair of disc faces, an inlet and an outlet was provided for flushing that groove. The "cleaning channel" thus defined did not function to clean the engaged surfaces when rinse liquid was directed thereinto. The rinse liquid was injected for the purpose of flushing the channel of any residue which may have collected therein. In fact, disassembly remained a pre-requisite to cleaning of the frictionally engaged disc surfaces. It should be pointed out that there was no means available by which the frictionally engaged disc surfaces could be cleaned in the absence of disassembly.

SUMMARY OF THE INVENTION

The herein invention provides a liquid sampling, metering and transfer valve assembly having means whereby both liquid sample and diluent are metered within the valve assembly. The valve assembly includes means defining a pair of segmenting passageways formed in the center, rotatable valve disc and plural complementary matching or counterpart passageways in the outer stationary valve discs, the discs arranged coaxially aligned and mounted on a spindle with the center disc having opposite faces frictionally engaged with the faces of the sandwiching outer or stationary valve discs. The center valve disc also provided with an additional segmenting passageway arranged for cooperation with associated or counterpart passageways formed in the stationary discs. Loops having precise interior volumes are secured to one of the stationary discs, each for containing a diluent volume required for combination with respective precise volume isolated in the segmenting passageways.

The valve assembly of the invention is characterized by the provision of means whereby a continuous body of sample is introduced into and through the valve assembly defining a continuous flow path including through the first mentioned segmenting passageways, the valve operating stepwise to isolate a precise volume of said sample in said segmenting passageways and then functioning to deliver the content of one of the said passageways to a location exterior of the valve assembly along with the content of one of the loops. The other one of the first mentioned segmenting passageways contains a precise volume of the sample which is stored therewithin for further operation. The valve then operates stepwise to enable the return to the valve and into the third segmenting passageway of at least a portion of the dilution formed when the content of the one segmenting passageway with diluent is delivered to the location exterior of the valve assembly. The valve assembly operates then to isolate a segment of the said returned dilution, which is delivered, along with the content of a second of the loops, to a testing location. Simultaneously, the stored volume of sample is delivered from the other one of the first mentioned segmenting passageways, along with the content of the remaining loop, to another testing location, internal channel means having an inlet and outlet are provided whereby rinse liquid can be introduced into the valve assembly for cleaning the frictionally engaged facing surfaces within the valve during rotation of the center disc thereof, a 360 degree rotation of said center disc can be employed as a shut-down or pre-start-up rinsing step.

DESCRIPTION OF A PREFERRED EMBODIMENT

Figure 1:
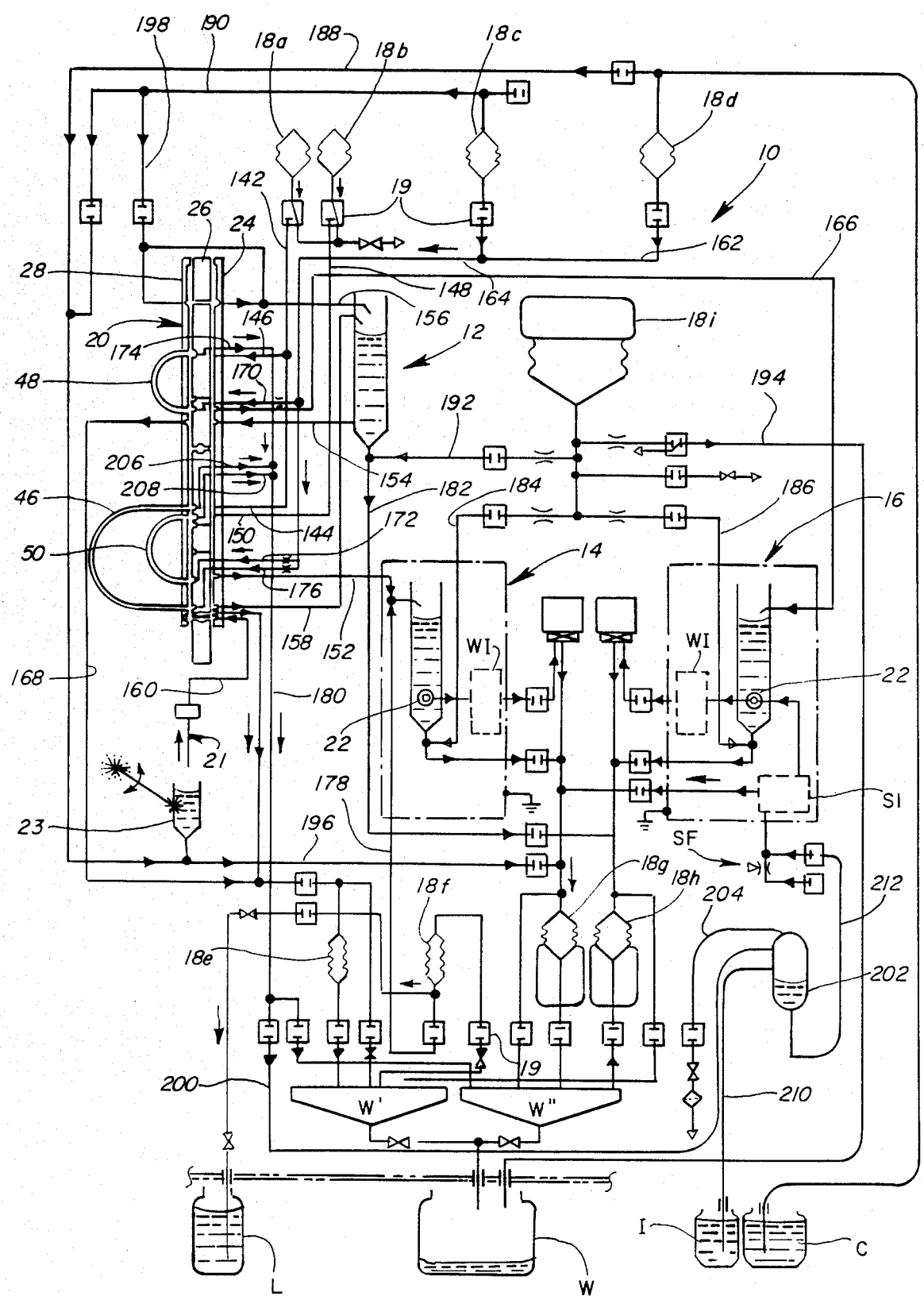
FIG. 1 is a schematic representation of a blood analysis system employing the liquid sampling, metering and transfer valve assembly constructed in accordance with the herein invention.

Referring now to the drawing, the liquid sampling, metering and transfer valve assembly according to the invention is illustrated diagrammatically in FIG. 1 as utilized in a blood analyzing system 10 and is designated generally by reference character 20. In addition to the valve assembly 20, the system 10 includes a pre-dilution chamber 12; a testing apparatus 14 here dedicated to determining certain characteristics of white blood cells; a testing apparatus 16, here dedicated to determining certain characteristics of red blood cells; a transfer pump 18a for effecting the transfer of a sample from the valve assembly 20 to the pre-dilution chamber 12, as required and a transfer pump 18b for effecting the transfer of a properly diluted sample from the valve assembly 20 to the testing apparatus 16, as required. Transfer pumps 18c and 18d respectively, effect delivery of suitable diluent and cleaner to the valve assembly 20 and from there, to the desired locations within the system 10. Pump 18e is provided to control movement of fluids and liquids for aspiration of the original liquid sample from its source (not shown) to the valve assembly 20 and or the dilution in the pre-dilution chamber 12 to the valve assembly 20 at the proper time in the operational program of the system 10. The valve assembly, in turn, operates to segment and isolate therein a portion of the dilution obtained from the chamber 12. The pump 18d also operates to direct an isolated dilution portion from the valve assembly to the testing apparatus 14. Pump 18f operates to direct a liquid lysing reagent from a source L thereof to the testing apparatus 14 at a proper time in the program of the system 10. Pumps 18g and 18h operate to move the diluted samples within the testing apparatus 14 and 16 respectively, through the sensing means 22 thereof. Pump 18i operates to mix the liquids within testing apparatus 14 and 16. A waste reservoir W also is provided. Suitable conduits are provided leading to and between the various mentioned components of the system 10. In FIG. 1 there are illustrated a plurality of pinch valves represented diagrammatically by reference characters 19, respectively but not all so identified in the FIGURE. The testing apparatus 14 and 16 each includes a suitable sweep isolator SI.

Aspirator probe 21 is provided for drawing an original liquid sample from a source thereof (not shown) for direction to the valve assembly 20 while a backwash or wash cup 23 is provided to be positioned vertically aligned with the probe once the sample has been drawn, and is continued in that aligned condition through the backwash and rinse steps of the system 10. The wash cup 23 otherwise is offset from the probe 21.

The liquid sampling, metering and transfer valve assembly 20 according to the herein invention comprises a pair of coaxially aligned outer stationary valve disc elements 24 and 28 having a rotatably movable central or inner valve disc element 26 sandwiched therebetween. The stationary elements 24 and 28 are arranged spaced apart only sufficiently to accommodate the central element 26 therebetween. The outer stationary valve disc element 24 shall be referred to as the front element of the assembly 20 as utilized in the system 10. Likewise, the outer stationary valve disc element 28 shall be referred to as the rear element of the assembly 20, again conforming to the preferred disposition thereof when the assembly 20 is mounted for utilization in the system 10.

The front element 24 is provided with opposite, parallel faces 24' and 24''. The rear element 28 also is provided with opposite, parallel faces 28' and 28''. The central or inner element likewise has opposite, parallel faces 26' and 26''. The elements 24, 26 and 28 preferably are formed from a suitable ceramic material with the facing surfaces thereof polished and formed precisely flat to within one or two Helium bands so as to reduce wear as well as friction and bending when the respective elements are assembled and the elements arranged so that the respective facing surfaces are frictionally engaged and the central element rotated relative to the others during the operation of the valve assembly 20.

Each of the valve disc elements 24, 26 and 28 have a central axial passageway 30, 30' and 30'' respectively, of the same inner diameter, the centers of which are aligned when the valve assembly 20 is assembled and mounted for fluid handling during the operation of the system 10. The valve assembly 20 preferably is multipositional and mounted so as to be driven, for example, by a stepper motor via a worm gear drive (both not shown). Each of the valve disc elements 24, 26 and 28 carry an outwardly opening notch 32, 34 and 36 respectively across the outer perimetric surface 38 thereof for the purpose of guiding the elements in alignment. Additionally, each of the valve disc elements 24, 26 and 28 carries an outwardly opening, thin reference slot 40, 42 and 44 respectively at a selected location across the outer perimetric surface 38, the center cross-lines of the notches 32, 34 and 38 are aligned and, as well, the reference slots 40, 42 and 44 also are aligned, conveniently via the use of a thin precision blade (not shown), to assure accurate location of the home or initiate position assumed by the valve disc elements 24, 26 and 28 each relative to the others, as will be described hereinafter.

The front valve disc element 24 provides means which function to establish communication to and from the various fluid and liquid sources and the delivery destinations within the system 10 and carries plural axially parallel precision passageways (bores) in groups to cooperate with selected precision parallel passageways formed on the central and rear valve disc elements 26 and 28 to define plural, generally parallel fluid paths axially through the assembled valve disc elements 24, 26 and 28 of the valve assembly 20 within the system 10. The rear valve disc element 28 carries three hollow loops 46, 48 and 50 secured tightly, sealingly thereto, each of which is formed with a precise interior volume and communicates to precision passageways formed in that element 28.

The central valve disc element 26 is rotatable, selectively, in precise serial steps in accordance with the program of the system 10 and carries a pair of segmenting passageways 52, 54 defining measuring chambers for isolating precise volumes of the original liquid sample from the flow path thereof through the valve assembly 20 established when said liquid sample is aspirated from the source of said sample via the aspirator probe 21, said isolation occurring when the central valve disc element 26 also carries plural, axially parallel passageways to bridge matching axially parallel passageways formed in both of the stationary valve disc elements 24 and 28 as the central valve disc element 26 is rotated through its stepwise rotational movement during the operation of the valve assembly 20 in accordance with the predefined program of the system 10. Rotation of the central valve disc element 26 additionally isolates a precise volume of diluent within each of the loops 46, 48 and 50. The respective valve disc elements 24, 26 and 28 are formed to enable a neutral position to be reached whereat the only communication between the valve assembly 20 and the exterior thereof during one step in the program of said system 10 is via the washing channels to be described hereinafter.

Figure 2A:
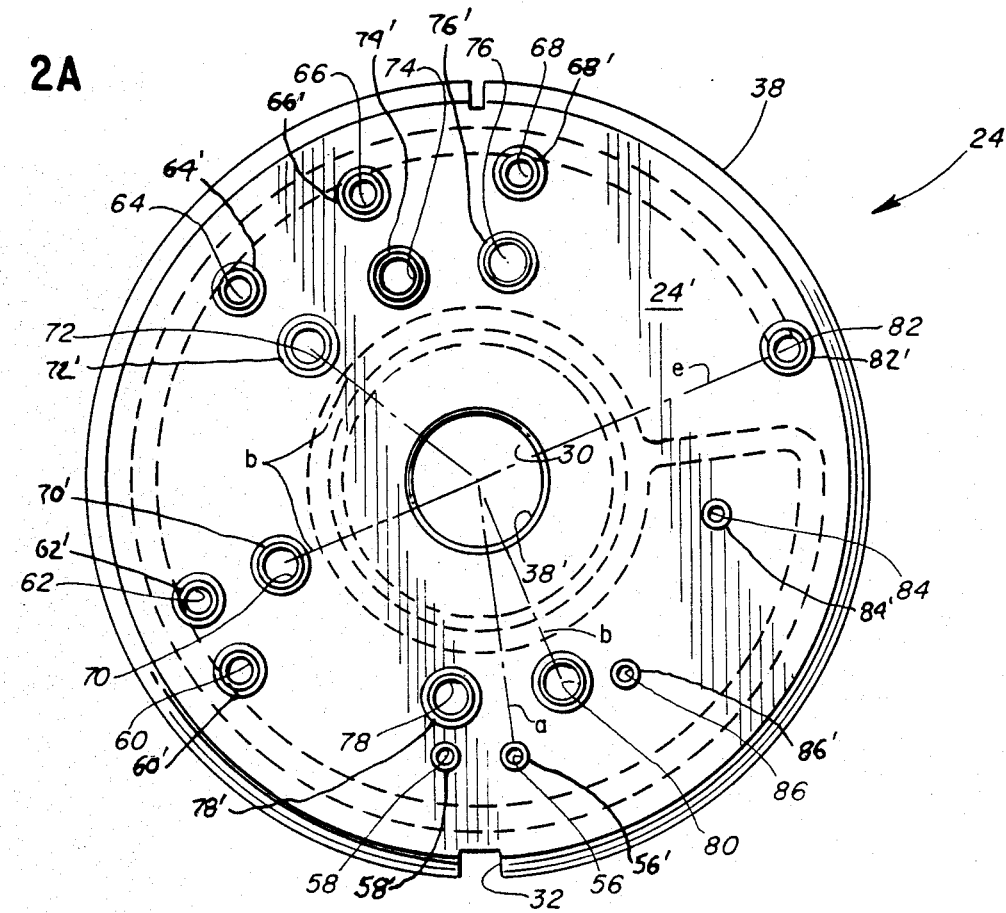
FIGS. 2A and 2B are plan views of the front valve disc element of the valve assembly according to the invention, FIG. 2A illustrating the outer face thereof and FIG. 2B illustrating the inner face thereof.
Figure 2B:
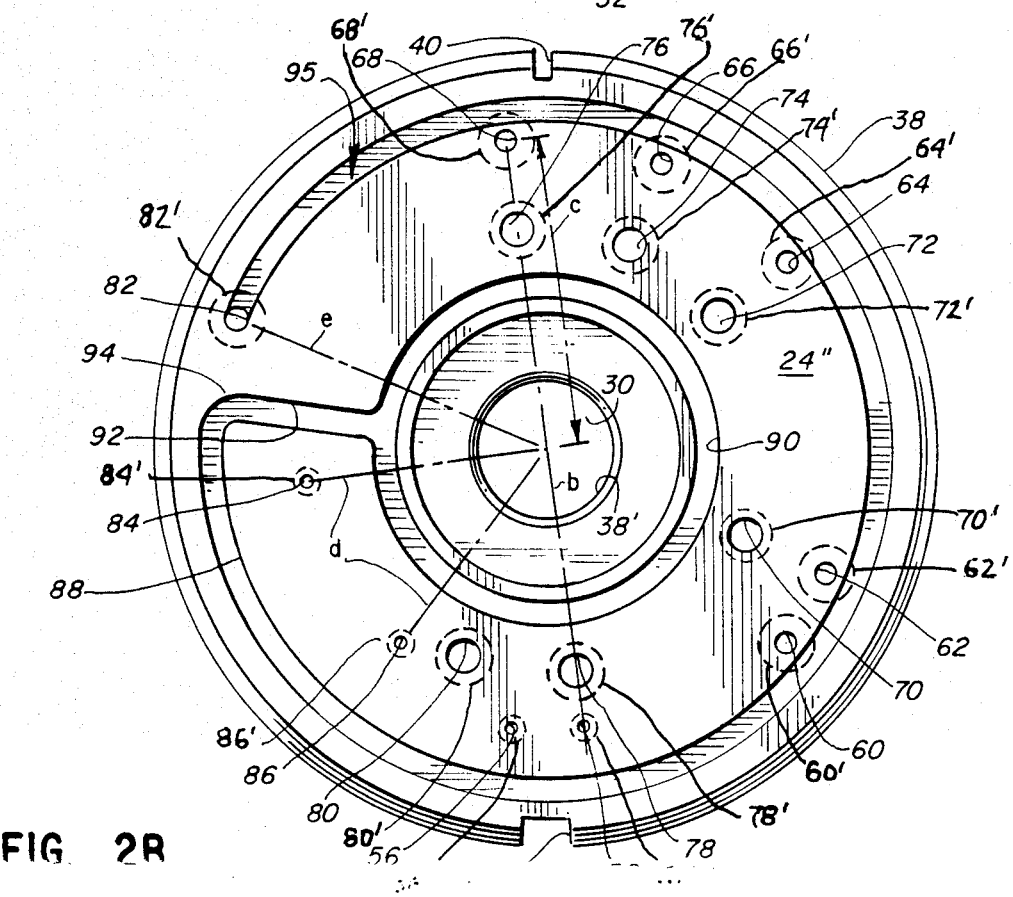

The three valve disc elements 24, 26 and 28 shall be described with reference to FIGS. 2A and 2B, 3A and 3B and 4A AND 4B, respectively. FIGS. 2A & 2B illustrate the front valve disc element 24, positioned with the outer face 24' illustrated in FIG. 2A and with the inner face 24'' illustrated in FIG. 2B.

Referring first to FIG. 2A, the front valve disc element 24 carries a first set (pair) of angularly spaced, axially parallel, through passageways 56 and 58 of precise, preferably uniform inner diameter, the centers of which being angularly spaced apart 15 degrees and at the same radial distance "a" from the center of axial passageway 30 of said element 24. A second set (pair) of angularly spaced, axially parallel, through passageways 60 and 62 are formed in said element 24. The passageways 60 and 62 have precise, preferably uniform inner diameters. The centers of passageways 60 and 62 are spaced angularly 15 degrees one from the other with the passageway 60 being angularly spaced forty-five degrees from the center of passageway 58; the radial distance between the respective centers of passageways 60 and 62 and the center of axial passageway 30 being "c". A third set of axially parallel, angularly spaced through passageways 64, 66 and 68 are formed in the front valve disc element 24 with their respective axial centers being angularly spaced equally one from the other an angular distance of 30 degrees with the axial center of passageway 64 being at an angular distance of 60 degrees from the axial center of passageway 62d. The axial centers of each of the passageways 64, 66 and 68 are spaced a radial distance of "c" from the axial center of passageway 30. Accordingly, the axial centers of passageways 60, 62, 64, 66 and 68 intersect a circular line taken concentric with the axial passageway 30 and spaced a radial distance of "c" from the axial center of said passageway 30.

An axially parallel through passageway 70 is formed in the front element 24 angularly spaced 60 degrees from the axial center of passageway 78 and parallel thereto, spaced a radial distance "b" from the axial center of passageway 30 and along a line taken through the axial centers of passageways 30 and 62.

A fourth set of axially parallel, through passageways 72, 74 and 76 is formed in the front element 24, the axial centers of each lying respectively, along lines taken through the axial centers of passageways 30 and 64, 66 and 68 respectively; the axial centers of said last mentioned passageways also being spaced angularly 30 degrees one from the other and each also being at a radial distance "b" from the axial center of passageway 30.

A fifth set (pair) of axially parallel, angularly spaced through passageways 78 and 80 are formed in said front element 24, the axial centers thereof being angularly spaced apart 30 degrees and the axial center of each passageway 78 and 80 being spaced a radial distance "b" from the axial center of passageway 30; the axial center of passageway 78 lying along a line taken through the axial centers of passageways 30 and 62.

The axial centers of passageways 78 and 80, as well as the axial centers of passageways 70, 72, 74 and 76 all lying in a second circular line drawn concentrically with passageway 30, the radius of said circular line being "b".

A sixth set of axially parallel, through passageways consisting of passageways 84 and 86 is formed in the front element parallel to and having the same diameter as the axially parallel passageways 56 and 58. The axial center of passageway 84 is spaced a radial distance "d" from the axial center of passageway 30. Likewise, the axial center of passageway 86 is spaced a radial distance "d" from the axial center of passageway 30 and is angularly spaced 15 degrees from a line taken through the axial centers of passageways 80 and 30. The axial center of passageway 84 is angularly spaced 60 degrees from a line taken through the axial centers of passageways 80 and 30 (and is angularly spaced 45 degrees from a line taken through the axial centers of passageways 86 and 30).

A singular axially parallel through passageway 82 is formed in the front element 24. The axial center of passageway 82 is located along a line taken diametrically through the axial centers of passageways 62, 70 and 30 and is located between the axial center of passageway 30 and the perimetric surface 38 of said element 24 at a radial distanced "e" from the axial center of passageway 30. All the axially parallel passageways formed in the valve disc element 24 are parallel to the center axis of said element as well as to themselves. All of the axially parallel passageways formed in said valve disc element 24 communicate to the exterior of the valve assembly 20 by respective nipples indicated in the drawing by priming of the reference characters identifying the said axially parallel passageways, the said axially parallel passageways opening to the opposite surfaces 24' and 24" of said element. The nipples are adapted to be received in the open ends of suitable conduits, to be described later, for communication to the exterior of the valve assembly 20.

Referring to FIG. 2B, the inner surface 24' carries a pair of concentric circular grooves 88 and 90, groove 88 comprising the outer groove and groove 90 comprising the inner groove. Groove 88 extends circumferentially substantially about 350 degrees spaced inwardly of the perimetric surface 38 of said element 24 while the inner groove 90 is endless and is spaced from of the inner perimetric surface 38' of the element 24 surrounding the axial passageway 30 thereof. Grooves 88 and 90 are connected or linked by radial groove 92 including a linking arcuate groove 94. The opening of passageway 82 to the surface 24" is located at the free end 88' of the outer groove 88, the center of passageway 82 being coincident with the center line of the groove 88

Figures 3A, 3B:
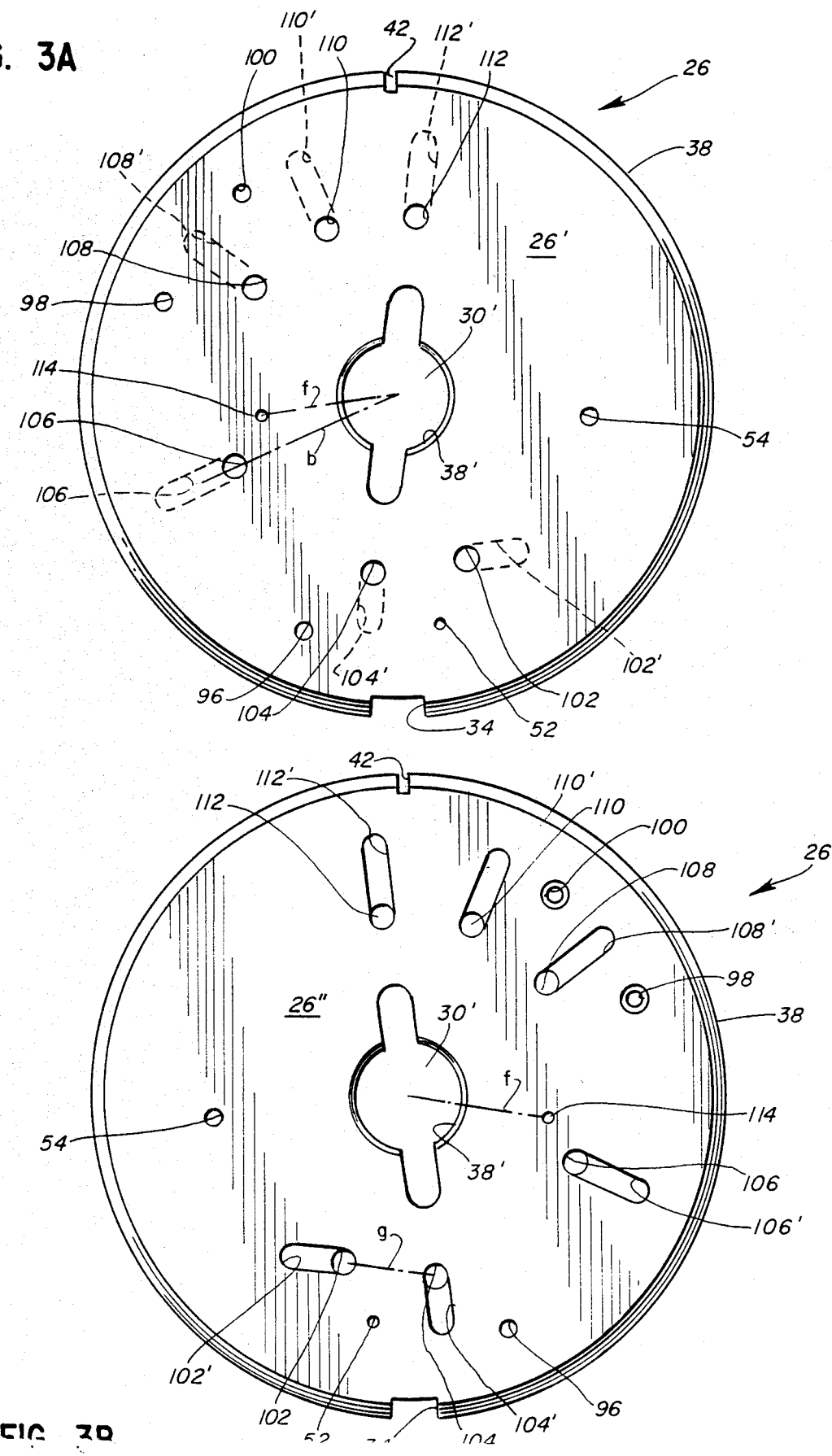
FIGS. 3A and 3B are plan views of the center valve disc element of the valve assembly according to the invention, FIG. 3A illustrating one surface thereof which faces the inner face of the front valve disc element when the valve assembly is assembled and FIG. 3B illustrating the opposite surface thereof.

Now, attention is directed to FIGS. 3A and 3B wherein the central valve disc member 26 is illustrated, surface 26' being illustrated in FIG. 3A and surface 26" being illustrated in FIG. 3B. Referring to FIG. 3A, a pair of axially parallel, segmenting through passageways 52 and 54 are formed in the central element 26, the axial center of passageway 52 being spaced angularly from the axial center of passageway 54 by 75 degrees. Passageways 52 and 54 have identical uniform inner diameters (and identical to axial passageways 56, 58, 86 and 84 of valve disc element 24). An outer group of axially parallel, through passageways 96, 98 and 100 are formed in the central valve disc element 26 and have their center axis respectively intersecting a circular line taken concentrically with the axial passageway 30 of the central valve disc element 26 and having a radius "c". The center axis of passageway 96 is spaced angularly from the center axis of passageway 98 by 90 degrees determined from the angle defined by a line taken through the center axes of passageways 30' and 96, and a line taken through the center axes of passageways 30' and 98. Passageway 98 and passageway 100 are spaced apart angularly by 30 degrees as determined by the angle defined by a line taken through the center axes of passageways 30' and 98 and a line taken through the center axis of passageways 30' and 100.

A second group of axially parallel, through passageways 102, 104, 106, 108, 110 and 112 are formed in the center valve disc element 26, each opening to the opposite surfaces 26' and 26" thereof. The center axes of the second group of passageways intersect a circular line taken concentric with passageway 30' of element 26, said circular line having a radius "b". The axes of passageways 102 and 104 are spaced angularly one from the other by 15 degrees determined by the angle defined by a line taken through the axes of passageways 30' and 102 and a line taken through the axes of passageways' 30' and 104. The axes of passageways 104 and 106 are spaced apart an angular distance of 60 degrees determined by the angle defined by a line taken through the axes of passageways 30' and 104 and a line taken through the axes of passageways 30' and 106. The axes of passageways 106 and 108 are spaced apart an angular distance of 60 degrees determined by the angle defined by a line taken through the axes of passageways 30' and 106 and a line taken through the axes of passageways 30' and 108. The axes of passageways 108 and 110 are spaced apart an angular distance of 30 degrees determined by the angle defined by a line taken through the axes of passageways 30' and 108 and a line taken through the axes of passageways 30' and 110. The axes of passageways 110 and 112 are spaced apart an angular distance of 30 degrees determined by the angle defined by a line taken through the axes of passageways 30' and 110 and a line taken through the axes of passageways 30' and 112.

An axially parallel, through passageway 114 is formed in the center element 26 opening to opposite surfaces 26' and 26" of said center element 26. The center axis of passageway 114 is spaced a radial distance "f" from the center axis of passageway 30'.

Referring to FIG. 3B, oval configured, outwardly opening recesses or galleries 102', 104', 106', 108', 110' and 112' are formed in the center element 26 opening to the surface 26", the passageways 104, 106, 108, 110 and 112 open to the inner end of their respective gallery 104', 106', 108', 110' and 112'. These galleries each have their long axes coincident with a respective line taken through the axes of their respective passageways and the axis of passageway 30'. The shortest linear distance between the axes of passageways 102 and 104 is represented by a distance "g" along a line taken through said axes. The long axis of the gallery 102' is coincident with a straight extension along line "g'" from the line representing the distance "g". The long axis of each gallery 104', 106', 108", 110' and 112' lies in respective radial lines drawn through the center axis of passageway 30'.

Figure 4A:
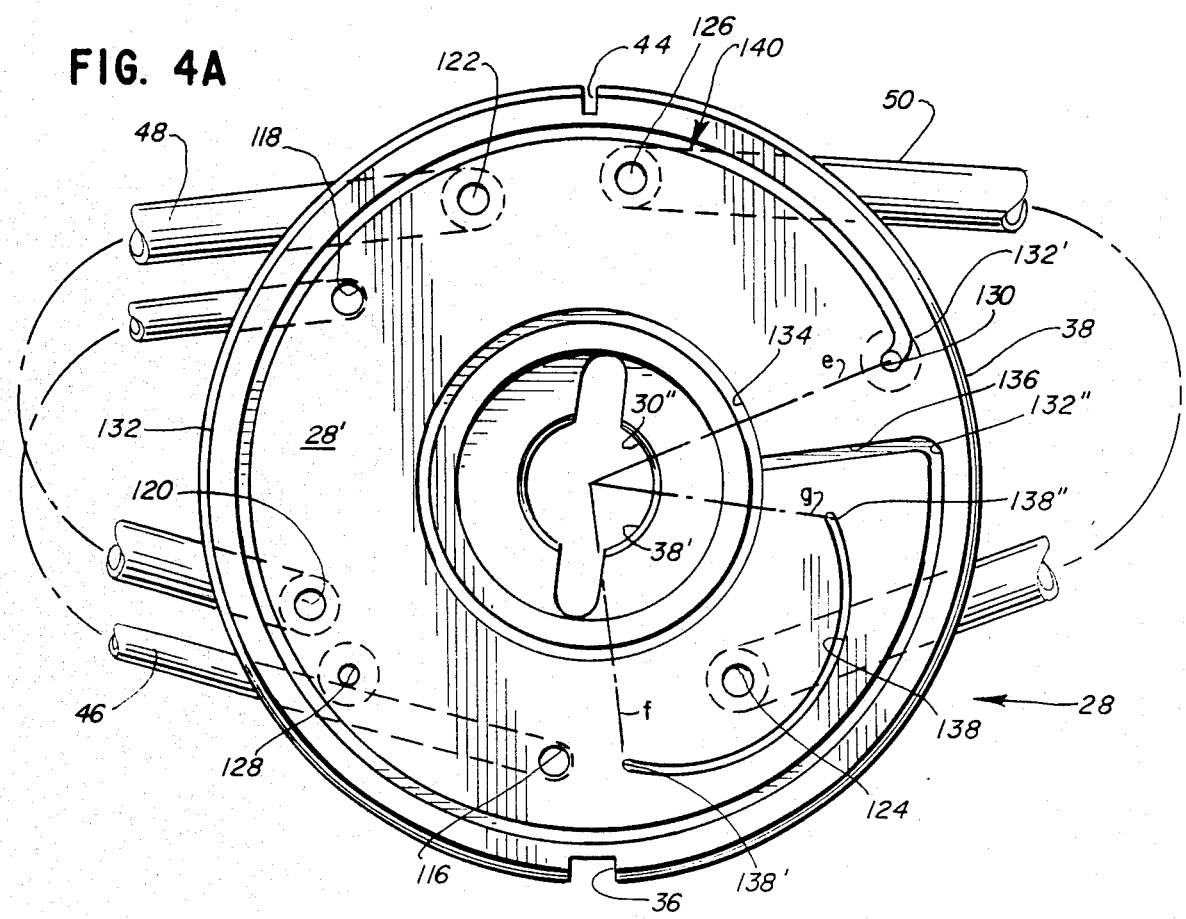
FIGS. 4A and 4B are plan views of the rear valve disc element of the valve assembly according to the invention, FIG. 4A illustrating the inner face thereof and FIG. 4B illustrating the opposite or outer face thereof; and, FIG. 5 is an exploded perspective representation of the valve assembly according to the herein invention.
Figure 4B:
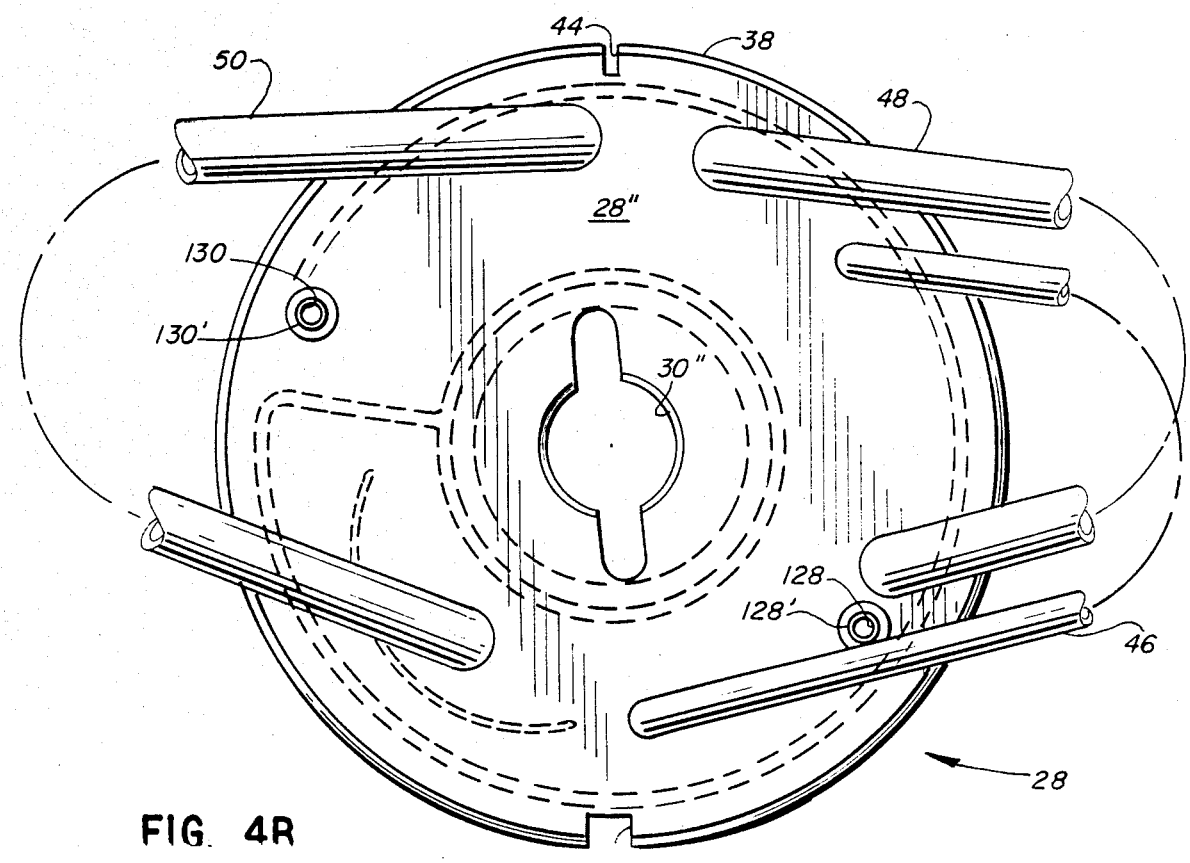
Figure 5:
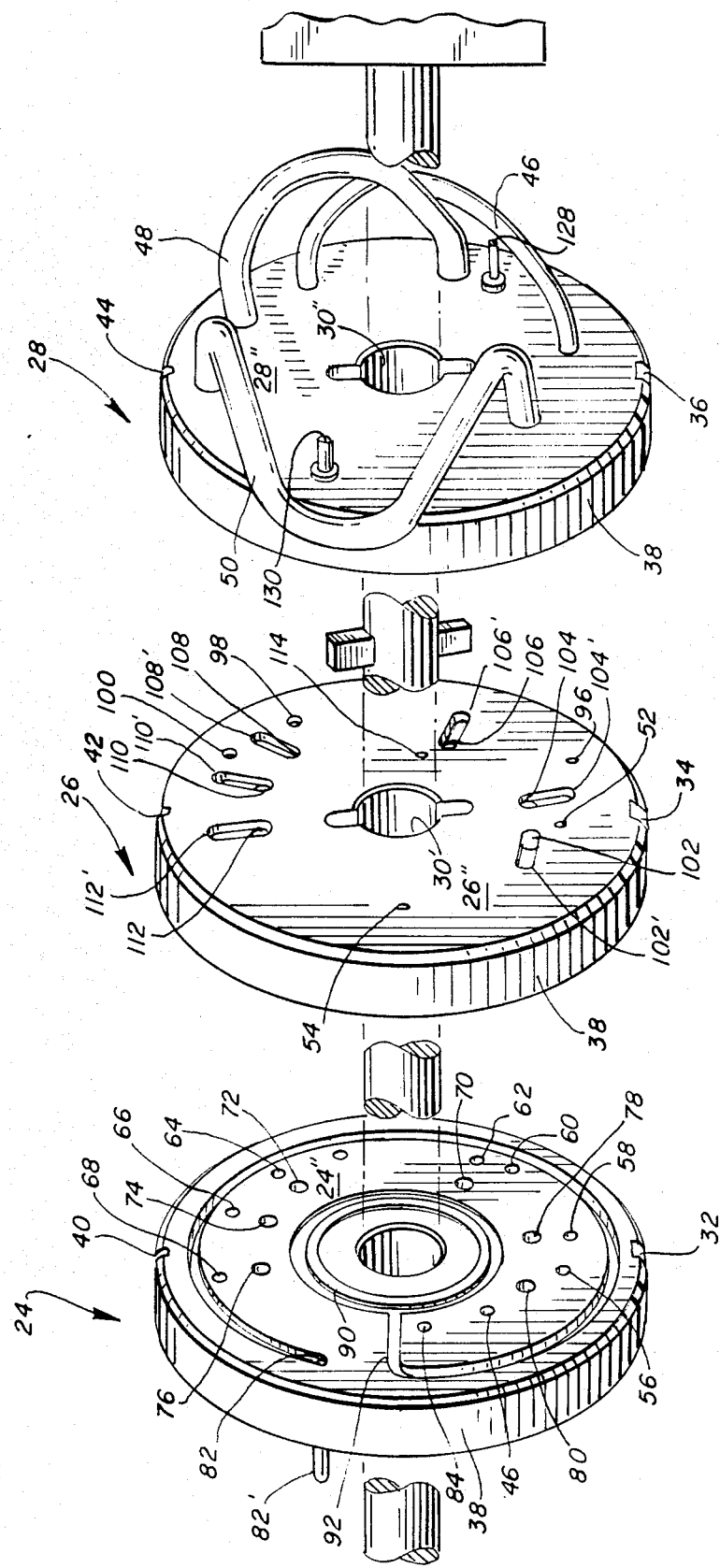

In FIGS. 4A & 4B, the rear valve disc element 28 is shown, viewing the inner face 28' thereof in FIG. 4A and viewing the outer face 28" in FIG. 4B. A first pair of axially parallel through passageways 116 and 118 is formed in rear element 28. A second pair of axially parallel through passageways 120 and 122 also is formed in said rear element 28 and a third pair of axially parallel through passageways 124 and 126 being formed in said element 28. As mentioned earlier, element 28 carries three hollow loops 46, 48 and 50 each having a precise interior volume and functioning to contain precise volumes of diluent. These loops are secured sealingly to said element 28 at the openings of the last mentioned passageways pairs to the outer surface 28", the loops being directed first outward of said surface 28" and then directed radially outwardly so as to minimize the space required to accommodate them at the rear of said valve assembly 20 when same is mounted for operation in the system 10.

Loop 48 has its opposite ends secured within passageways 120 and 122 while the loop 50 has its opposite ends secured within passageways 124 and 126. Additional axially parallel passageways 128 and 130 are formed in the element 28 opening to opposite faces 28' and 28" thereof. The passageway 120 is located so that its center axis is spaced 60 degrees from the center axis of passageway 116 as defined by a line taken through the center axes of passageway 116 and passageway 30" and a line taken through the axes of passageway 120 and the axial passageway 30°. The axial centers of both passageways 120 and 116 lie in the same circular line taken concentric with said axial passageway 30"; the axial centers of passageway 118, 122 and 126 also lying in the same circular line. The additional passageway 128 is located so that its center axis is spaced from the center axis of passageway 120 an angular distance of 15 degrees as defined by a line taken through the axial centers of passageways 30" and 128 and a line taken through the axial centers of passageways 30" and 120. The axial passageway 130 is located inwardly offset from the perimetric surface of element 28 and outwardly offset from the concentric circular line through which the axial centers of passageways 118, 120, 122, 124 and 128 lie. The liquid passing to and/or from opening of the hollow to the respective through passageway formed in the central element 26 is guided by the interior of respective gallery, the floor of which leads flow into the pertinent passageway entrance without turbulence as may occure if the flow was directly into the entrance to the said passageways.

An outer groove 132 is formed in the surface 28' of element 28 concentric with the axial passageway 30" of said element 28 and is spaced inwardly of the perimeter of said element, outer groove 132 extending about 350 degress circumferentially about the said perimetric surface. Concentric inner groove 134 is formed in the surface 28' concentric with both the outer groove 132 and the axial passageway 30, said inner groove 134 being endless. A linking radial groove 136 connects grooves 132 and 134 along a radial line taken through the axial center of passageway 30" and defining an angle of 15 degrees with the line taken through the axial centers of passageways 30" and 130. The groove 132 communicates with the passageway 130 by way of arcuate groove portion 132' and with the radial groove 136 by way of arcuate groove portion 132" at its opposite end. Grooves 132 and 134 define, with radial groove 136, a washing channel 140 with the imperforate portion of the surface 26" facing same; likewise, grooves 88, 90 and 94, along with the radial groove 92 formed in surface 24" also define a washing channel 95 with the imperforate portion of the surface 26' facing same.

A shallow, arcuate groove portion 138 is formed in the surface 28", one end 138' thereof located at a radial distance "f" from the axis of passageway 30" and the opposite end, 138", being located at a radial distance "g" from the axis of passageway 30". Ends 138' and 138" are located to align with the axial centers of passageways 52 and 54 respectively when the central valve disc element 26 assumes its "home" or initiate position with the reference slots 40, 42 and 44 aligned. As will be explained hereinafter, the passageway defined by groove 138 and the adjacent imperforate surface 26" serves to communicate between the passageways 52 and 54.

Attention now will be directed to the operation of the liquid sampling, metering and transfer valve assembly 20 once assembled and installed in the system 10. The valve assembly 20 is mounted so that the valve disc elements 24, 26 and 28 are arranged with surfaces 24", 26', 26" and 28' frictionally engaged respectively, only valve disc element 26 being rotatable while the other two valve disc elements 24 and 28 remaining stationary. Axial passageways 30, 30' and 30" are aligned and coaxial. The centers of each of the notches 32, 34 and 36 of elements 24, 26 and 28 respectively, are aligned and, as well, reference slots 40, 42 and 44 are aligned. When so mounted, the position of the valve assembly 20 is defined as the "home" or initiate position, particularly relating to the angular position assumed by the rotatable center valve disc element 26.

The valve assembly 20 operates through five positions which are defined by the relative relationship of the central valve disc element 26 to the stationary valve disc elements and in accordance with the operating program of the system 10. The "home" position is the initial mounting relationship of the three valve disc elements 24, 26 and 28. In addition to the alignment of the centers of the perimetric notches 32, 34 and 36 and the centers of the perimetric slots 40, 42 and 44, passageway 52 is aligned with passageway 56 and with the end 138' of arcuate groove 138. Passageway 54 is aligned with the passageway 84 and the opposite end 138" of arcuate groove 138. Passageways 52 and 54 serve as segmenting passageways or measuring chambers for isolating therein a precise metered measured volume (an aliquot of original liquid sample (the sample to be tested) when the central valve disc element 26 is rotated. Passageway 86 is aligned with passageway 104 and passageway 80 is aligned with passageway 102. Passageway 70 is aligned with passageway 106. Passageway 116 is aligned with the gallery 104' leading to passageway 104; passageway 118 is aligned with the gallery 108' leading to passageway 108; and, passageway 124 is aligned with the gallery 102' leading to passageway 102. At the "home" position, passageway 122 is aligned with the gallery 110' leading to passageway 110 while passageway 126 is aligned with the gallery 112' leading to passageway 112. Passageways 72, 74 and 76 are aligned with passageways 108, 110 and 112 respectively. Passageways 58 and 60 are blocked by the imperforate portions of the surface 26' of element 26. Passageway 80 is aligned with passageway 102. Passageways 64, 66 and 68 are blocked, again by the imperforate portions of said surface 26'. Passageways 96, 98, 100, 128 and 130 also are blocked, also by the imperforate surface of said face 26'. Thus, at the home position of the center valve disc element 26, the following flow paths through the valve are defined:

A. The flow path along passageway 56, through passageway 52 (of the center valve disc element 26), along arcuate groove 138 and through passageway 54 (of the central valve disc element 26) and then through passageway 84 of the front valve disc element 24.

B. The flow path along passageway 86, through passageway 104 along gallery 104' to passageway 116, through loop 46 to passageway 118 and thence, along the gallery 106' to passageway 108 to, and from passageway 108 passageway 72.

C. The flow path along passageway 80, through passageway 102, thence to gallery 102' leanding to passageway 124, from passageway 124 to and through loop 50 to passageway 126 and into gallery 112' leading to passageway 112 and from passageway 112 into and through passageway 76.

D. The flow path along passageway 74, through passageway 110, thence to gallery 110' leading to passageway 122, from passageway 122 to and through loop 48 to passageway 120 and thence to gallery 106' leading to passageway 106 and into and through passageway 70.

Thus, while the valve assembly 20 is at the home position, the system 10 operates to introduce diluent into the loops 46, 48 and 50 along paths B, C and D, during priming of the system 10. At the same time, original liquid sample is aspirated (or drawn) from a source thereof (a sample tube or other container brought into communication with the aspirator probe 21) into the value assembly along path A. Within the system 10, the sweep-flow means, including sweep isolator SI, adjunct to the testing apparatus, is primed, i.e. diluent being introduced thereinto, the testing apparatus 14 and 16 is being drained. If provided by the program of the system 10, can operate to aspirate air to dry the tip of the aspirator probe. Now, with the testing apparatus 14 and 16 having been drained and the loops 46, 48 and 50 primed (along with the predilution chamber 12 and testing apparatus 14 and 16), and with original liquid sample filling the flow path A through the valve assembly, the center valve disc element 26 is operated to rotate 15 degrees to place the valve assembly 20 in operating position #1. The drainage of the predilution chamber 12, the backwash cup 23 is brought to a disposition with its entry vertically aligned with the aspirator probe 21 and filled. In position #1, the rotation of the center valve disc element 26 effectively isolates the content of passageway 52 and the content of passageway 54 from the flow path A and thus isolates a precise volume of the original sample in each passageway 52 and 54. Each of these isolated sample volumes can be described as "aliquots".

While the valve assembly 20 is disposed in position #1, passageway 52 is aligned with passageway 58 of valve disc element 24. Passageway 52, in the center valve disc element 26, is in alignment with passageway 116. A passageway 98 is aligned with passageway 118 and also is aligned with passageway 64. The passageway 52 becomes a portion of the flow path which includes the loop 46, the pre-dilution loop. Passageway 100 is aligned with passageway 122 but is blocked by the surface 24" of valve disc element 24. The passageway 80 is blocked, as are passageways 60, 62, 74, 76, 110, 108, 86, 84, 80, 54, 102, 126, 104 and 96. Passageway 66 is aligned with passageway 100 which is in turn aligned with the passageway 122 and loop 48. However, the opposite end of loop 48 is coupled to passageway 120 which is blocked by surface 26" of the center valve disc element 26. Therefore, the diluent content of the pre-dilution loop 12 long with the measured, precise volume of original liquid sample which was isolated in the passageway (or chamber) 52. The draining of the testing apparatus 14 and 16 is completed and when the program of the system 10 effects a further fifteen degree rotation of the valve disc element 26 to place said assembly 20 into the second position of operation, the position #2.

When the valve assembly 20 is disposed in the second position, vacuum is drawn by the aspirator pump 21 to introduce the completed pre-dilution from the pre-dilution chamber 12 back into the valve assembly 20 and the system further operates to drain the pre-dilution chamber 12, leading its remaining content to a waste reservoir W. With the valve assembly 20 disposed in the second position, passageways 56 and 58 are blocked. Passageway 60 is aligned with passageway 96 which is aligned with passageway 128. Passageways 62, 70, 72, 64, 66, 100, 112, 84, 86 and 80 are blocked. Passageway 74 is aligned with passageway 108, in turn aligned with gallery 108' leading to passageway 122. Passageway 76 is aligned with passageway 110, in turn aligned with gallery 110' leading to passageway 128. Passageways 124 and 126 are blocked so that the content of the loop 50 is isolated. The passageways 120 and 122 remain blocked so that the content of loop 48 remains isolated. The pre-dilution chamber 12 is rinsed. Now, the program of the system 10 operates to rotate the center valve disc element 26 a further 15 degrees, making a total rotation of 45 degrees to place the valve assembly 20 in position #3.

When the valve disc element 26 rotates to position #3, a precise volume of the pre-dilution is isolated in the passageway 96 (same functioning as a measuring chamber for the pre-dilution). Now the system operates to drive the volume in passageway 96 and the original liquid sample (which had been stored in passageway 54) to the testing apparatus 14 and the testing apparatus 16 respectively, along with the content of loop 48 and 50 respectively, mixing of the isolated volumes (or aliquots) and their respective diluent volumes in the respective testing apparatus being effected (by pump 18i). The system 10 operates via pump 18f, to deliver lyse reagent from the source L to the testing apparatus 14 so that a determination of the characteristics of the white blood cells therein may be made in testing apparatus 14. A determination of the red cell characteristics is ready to be made in testing apparatus 16. While the mixing occurs, the center valve disc element 26 is caused to rotate 50 degrees in the reverse direction relative its prior rotative activity during its progens through the 1st through 3rd positions from the "home" position so that the center valve disc 26 arrives at a position 5 degrees further than its "home" position.

Rotation of the valve disc element 26 from its position #2 to its disposition in position #3 places passageways 86 and 54 aligned with the passageway 124 and passageways 62 and 96 aligned with the passageway 120. Passageways 66 and 98 are aligned with passageway 122 and passageways 68 and 100 are aligned with passageway 126. The content of passageway 54 is directed to the testing apparatus 16 along with the diluent content of loop 50. The content of passageway 96 is directed along with the diluent content of loop 48 to the testing apparatus 14.

With the valve disc element 26 reverse rotated to its position #4. that is, 5 degrees past its "home" position, the system 10 operates to retain the valve disc element 26 in a "dwell" condition, initiating a one second "sweep-flow" purge just before the "counting" or testing is initiated. After the "purge" period, the center valve disc element 26 is caused to rotate toward the "home" position during which rotation testing is initiated and completed at the time the valve disc element 26 arrivces at the "home" position.

When the center valve disc element 26 returns to the "home" position, the testing is completed, the backwash cup 23 is raised so that the aspirator probe 21 is disposed within the said backwash cup 23. Diluent then is aspirated from the backwash cup 23 into the aspirator probe 21 and then proceeds along the same path taken by the original liquid sample. At the same time, the loops 46, 48 and 50 are primed with diluent and the pre-dilution chamber 12 is filled with diluent.

The valve disc element 26 then is rotated 15 degrees to the first portion of the valve assembly 20. The content (now diluent) of passageway 52 is directed to the pre-dilution chamber 12. A second volume of diluent is withdrawn (by aspiration) from the backwash cup 23 to complete cleaning of the aspirator probe 21. The backwash cup 23 is lowered, thereby causing wiper means (not shown) to translate downwards relative to the probe 21 to clean and dry the exterior of the probe 21. Optionally, air (or vacuum) can be drawn and applied to the tip of the probe 21 to dry same. The center valve disc element 26 then rotates to assume the 2nd position whereat diluent is pumped to drive the isolated first dilution from the pre-dilution chamber through the pertinent passageways of the valve assembly 20 to the testing apparatus 14 and 16 respectively.

The center valve disc element 26 then is rotated to its position #3 whereat diluent is driven to the testing apparatus 14 and 16. The valve disc element 26 then returns to the "home" position. The described rinsing operation of the valve assembly 20 and the respective backwash cup, predilution chamber and testing apparatus is repeated. With the valve disc element 23 returned to its "home" position, the system 10 is ready for the next orignial liquid sample.

The valve assembly 20 is provided with means therewithin whereby the interior surfaces of the valve disc elements are washed, normally occuring at the time the system is shut down, as after a day's operation. A source of cleaning liquid and a source of air is coupled respectively to passageways 82 and 130 (FIGS. 2A and 4A) or vice versa. At a signal, the system 10 operates pumps 18d and 18e to direct cleaning liquid and air respectively serially into, say passageway 130. The valve disc element 26 begins a continuous rotation through 360 degrees while the cleaning liquid courses into and through wash channel 132 along radial channel 136 to and through endless channel 134 to passageway 114. The cleaning liquid continues to flow through passageway 114 and enters the endless channel 90, passes along channel 92 to the outer wash channel 88 to exit the valve assembly 20 at 82. The wash channels are enclosed by the facing surfaces 24″ and 28′. The surfaces 24″ and 28″ as well as surfaces 26′ and 26″ are washed by the cleaning liquid passing through the radial channel portions 130 and as the center valve disc 26 rotates through the 360 degree full rotation. Additionally, the inner and outer grooves 88 and 92, and 132 and 134 prevent any debris or liquid emerging from the junctures of any of the passageways from traversing along the frictionally engaged interior surfaces from reaching the circumferential surfaces of the valve assembly 20, any such material being caught by the grooves and washed away with the flow of cleaning liquid through the channels 140 and 95.

With particular reference to FIG. 1, a description of the operation of the valve assembly 20 shall ensue following the flow of fluids through the system 10 from the valve assembly 20 along the respective conduits to the various pumps, chambers, testing apparatus, i.e. destinations in said system at each stepped position of the said valve assembly 20.

With the valve assembly 20 at the "home" position, original liquid sample, in this system, whole blood, is aspirated through the aspirator probe 21 along conduit 160 to the valve assembly 20. The loops 46, 48 and 50 are primed, that is, filled with diluent employeing pump 18c following conduit 164 and branching by way of conduits 170, 172 and 176 to the valve assembly 20. Air pressure moving ahead of the diluent travels outward from the valve assembly 20 along branch conduits 174, 206 and 208 to conduit 180 and then, via conduit to level detector 202 to conduit 204 returning to the source of pressurized air. The sweep flow SF also is primed, diluent from the source I following line 210 to level detector 202, and from detector 202 along line 212 to the sweep flow SF filling the sweep flow isolator SI with diluent, directing excess to the pump 18g to the waste chamber W′ and thence to the waste reservoir W.

The test apparatus 14 and 16 then are drained as is the pre-dilution chamber 12. Air then is aspirated from the system 10, including the aspirator probe 21.

The valve disc element 26 then is rotated to assume its position #1. The pre-dilution chamber 12 is drained via conduit 182 to pumps 18g and 18 h. With the valve disc element 26 still in the #1 position, the backwash cup 23, now in position vertically aligned with the probe 21, is filled with diluent. The rotation of the valve disc element 26 to position #1 from the "home" position, isolates a measured volume of the original sample and positions same to be directed to the pre-dilution chamber 12, along with the content of diluent contained in loop 46. This last mentioned delivery is effected by transfer pump 18a by air traveling from pump 18a along conduit 142 via conduit 144 to the loop 46 and via conduit 158 to the pre-dilution chamber 12. The mixing pump 18i directs air to the pre-dilution chamber 12 along conduit 192 for mixing the constituents within the pre-dilution chamber 12. Both the testing apparatus 14 and 16 are drained.

The valve disc element 26 of the valve assembly 20 is rotated to assume its 2nd position of operation and the predilued content of the predilution chamber is aspirated (drawn) from said chamber 12 to the valve assembly 20 following conduit 154, the flow passing from the valve assembly 20 to the aspirator pump 18e via conduit connection 168. The pump 18i then operates to effect the drained material is directed along conduit 182 to the pump 18h and from there, is directed to the waste chamber W" and teh waste reservoir W.

The valve disc element 26 then is rotated to assume position #3 of the valve assembly 20. Now, under the operation of the pump 18c, diluent is directed to the wash channels 140 and 95 of the valve assembly 20 and thence to the pre-dilution chamber 12 for rinsing of same. The rotation of said element 26 effects isolation of a given volume aliquot of said prediluted sample within the valve assembly 20. With the valve disc element 26 in position #3, pumps 18a, 18b and 18i operate to deliver the isolated predilution volume along with the content of loop 48 to the test apparatus 14 for mixing same therein. The pump 18a operates to deliver the originally isolated volume of original sample, along with the content of loop 50 to the testing apparatus 16 and mixed in said apparatus. Lyse reagent is delivered to the testing apparatus 14 and mixed with the content within said apparatus 14.

The valve disc element 26 next is rotated in a reverse direction from its prior rotational activity to assume a position 5 degrees past the "home" disposition. There the valve disc element 26 remains in a dwell state for a one second period. During this period, the sweep flow is purged. Then the program of the system 10 initiates the testing sequence, the pumps 18g and 18h operating to draw the respective contents of testing apparatus 14 and testing apparatus 16 through the scanning means 22 of the respective testing apparatus.

The valve disc element 26 begins to return to its "home" position when the testing is initiated and such testing is completed in the time elapsed until the "home" position is reached, terminating when said "home" position is reached.

Upon the valve disc element 21 reassuming its "home" position, the loops 46, 48 and 50 are once again primed. The backwash (diluent) content of the backwash cup 23 is aspirated through the probe 21 along conduit 160 into and through the valve assembly 20 so that the pre-dilution chamber 12 is rinsed. The backwash cup 23 is drained and then refilled. Next, the pre-dilution chamber 12 is drained following the previously described route. The refilled backwash cup 23 again is aspirated so that its content is again drawn into the probe and from there, through the valve. Then the testing appartus 14 and 16 is drained and the backwash cup 23 again is drained. The aspirator probe 21 then is rinsed and dried. Valve disc element 26 then rotates to its position #2 whereupon rinse liquid within the pre-dilution chamber 12 is drawn into the valve assembly 20 under the influence of the aspirator pump 18e, said rinse travelling through conduit 154 to the valve assembly and leaving the valve assembly via conduit 168 to the pump 18e and thence to waste chamber W', thence to waste reservoir W. The pre-dilution chamber 12 again is rinsed with diluent and the rinse then drawn through the valve for disposal to waste chamber W' and waste reservoir W.

Next, the valve disc element 26 is rotatably translated to its position #3 and diluent is directed to and from the valve assembly 20 via the loop 48 and into the testing apparatus 14 whereat it is mixed and the mixed content drained. Likewise, the apparatus 16 is rinsed along with the loop 50.

When the operational activity for a day has been completed and the apparatus 10 is to be shut down, the valve disc element 26 is caused to rotate 360 degrees and rinsed (cleaner liquid then diluent) is driven into the washing channels 95 and 140 during said rotation for cleaning of the engaged surfaces and of the content, if any, of the washing channels 95 and 140. Cleaning is effective due to the sweeping action of the rinse liquid particularly caused by rotation of the radial portions of said channels. The rinsing sequences preferably are carried out twice in succession to prevent any intermingling of samples, contamination within the system, over-runs and the like.

Thus there has been described a sampling, metering and transfer valve assembly which provides, for the first time, more than two internal segmenting passageways, each capable of containing an isolated precise aliquot of liquid sample, for distribution to exterior locations along with a precise, measured volume of liquid diluent. The valve further provides loops as a part of the valve assembly each of which is capable of containing and storing a precise volume of diluent. There also has been described means whereby an aliquot of liquid sample is directed to a location exterior of the valve assembly with diluent to form thereat a diluted body of liquid, said body being returned to the valve assembly and, therein, an aliquot thereof is isolated and directed from the valve assembly with a given volume of diluent to a testing location. The valve assembly described is also capable of retaining an aliquot of liquid sample for sebsequent distribution (with a precise volume of dilent) to an exterior located testing apparatus. All the steps of metering of the liquids are performed within the valve assembly described.

All of the steps described above are capable of being effected without operator interaction, automatically and accurately.

In the preferred embodiment described herein, the hollow loop 46 contains 600 microliters of diluent, the hollow loop 48 contains 1800 microliters of diluent and the hollow loop 50 contains 1450 microliters of diluent. The pre-dilution initially obtaineld in pre-dilution chamber 12 is a 1:75 dilution. The dilution delivered to the testing apparatus 14 and tested therein is a 1:250 dilution when lyse reagent is added. The dilution delivered to the testing apparatus 16 and tested therein is a 1:6250 dilution. The aforementioned volumes and degrees of dilution are examples and are not intended to be limiting with respect to the scope of the invention.

In the course of the above description, there have been many references to the terms "axially parallel" and "matching" as applied to the internal passageways formed in the valve disc elements 24, 26 and 28 of the valve assembly acocrding to the herein invention. The term "axially parallel" is intended to describe passageways in the form of bores which are formed through the thickness of the discs which are assembled side by side and mounted to a spindle or the like, the said bores opening to the opposite faces of the discs in which they are formed. These passageways so described are parallel to the center axis of the respective disc in which they are formed, and, their center axes are parallel to each other. Each of the through passageways described in a particular disc has counterpart passageways which comprise bores formed in the other discs, the important criterion being that by "matching" describes a counterpart which is aligned with and communicates fully with its counterpart bore. By following the description of the respective flow paths for liquid sample and for diluent, as well as those paths leading into land out of the valve assembly to the pre-dilution chamber, the testing apparatus 14 and 16, to the sources of liquid sample and diluent and those leading to other destinations to and from the valve assembly 20 will clearly enable the reader to indentify which passageways are included in particular matching relationships. "Matching" passageways are defined as counterparts to the specific passageways indentified.

It should be recognized that the scope of the invention herein described is intended to include through passageway pairs, including so-called segmenting passageways, which may be diagonal relative to the center axis of the discs and may not be identically parallel to one another. So long as they function to carry flow to and from their counterpart passageways in the other discs, they would be considered to be within the scope of the invention if their content is entirely received from and passed through the respective counterpart or "matching" passageway. Additionally, reference in the appended claims to "aliquot" is intended to describe that volume of liquid which is isolated within the segmenting passageways regardless of its identity, either as original liquid sample or as the product of the pre-dilution step which is returned to the valve assembly 20 from the pre-dilution chamber 12 and a precise volume of which is isolated within the segmenting passageway (or measuring chamber) 96 and subsequently diluted and directed to the testing apparatus 14.

Many alternate structures can be devised and many variations made in these structures as well as those illustrated and described herein without departing from the spirit and scope of the invention as set forth in the appended claims.

What we claim is:

1. A liquid sampling, metering and transfer valve assembly for use in diluting apparatus of the type employed in a particle study system, the valve assembly being capable of providing plural precise liquid sample volumes from a single liquid source, said valve assembly including internal segmenting passageways for measuring, isolating and storing precise liquid sample aliquots therein, means for delivering each aliquot to different locations exterior of said valve assembly along with respective precise volumes of liquid diluent as individual dilutions, each dilution being of predetermined concentrations and loop means integral with said valve assembly for measuring, isolating and storing each of said precise volumes of liquid diluent as individual volumes for delivery to each respective one of said aliquots as said individual dilutions.

2. A liquid sampling, metering and transfer valve assembly for use in diluting apparatus of the type employed in a particle study system, said valve assembly capable of providing plural precise measured volumes of liquid sample from a single source thereof as individual aliquots simultaneously metered and isolated within said valve assembly from a continuous body of the liquid sample along a serial path defined therein and delivering each aliquot to a predetermined locations exterior of said valve assembly along with a predetermined volume of diluent to form plural individual dilutions of precise concentration respectively thereat, means forming and integral part of said valve assembly for metering, isolating and storing therewithin individual precise volumes of diluent for delivery to said respective aliquots, all metering being performed within said valve assembly.

3. The valve assembly according to claims 1h or 2 wherein said valve assembly includes a pair of spaced outer stationary valve disc elements and an inner rotatable valve disc element sandwiched therebetween, said inner valve disc element having opposite faces sealingly frictionally engaged with the adjacent faces of said outer element, plural internal segmenting passageways formed in said rotatable valve disc element, said loop means comprising plural hollow loops secured to an outer one of said stationary valve disc elements, each loop having a precise volume therein for isolating and storing a precise volume therein required to supply the diluent needed for one aliquot to form the desired dilutin therewith, there being one of said internal segementing passageways for each loop, plural first complementary counterpart passageways formed in one of said outer valve disc elements constructed and arranged for placement in communication with selected ones of said internal segmenting passageways sequentially upon step-wise rotation of said inner valve disc element for leading each aliquot into and out from said valve assembly and second complementary counterpart passageways formed in each of said inner and outer valve disc elements for leading diluent through said valve assembly following a path into and out from said segmenting passageways and including said loops whereby to make the respective dilutions of said respective aliquots to deliver the respective diluent and aliquot to the appropriate location, said loops capable of being loaded with diluent through said second complementary counterpart passageways and the volume therein being isolated upon rotation of said inner rotatable valve disc element.

4. The valve assembly according to claim 3 wherein the diluting apparatus includes aspiration means capable of being coupled to said valve assembly and a chamber exterior of said valve assembly containing a predeterimed volume of liquid diluent therein and another one of said segmenting passageways being capable of placement in communication with the exterior chamber at a time subsequent to isolation of an aliquot therein for delivery of said aliquot and the diluent content of one of said loops to the exterior chamber, said aspiration means capable of withdrawing a portion of the resulting content of the exterior chamber from the exterior chamber along a liquid flow path into and through an other one of said segmenting passageways and said first complementary passageways for isolation of an aliquot of the resulting content of the exterior chamber upon further rotation of said inner valve disc element, there being remaining a still other segmenting passageway containing an original aliquot of liquid sample retained therein and to be discharged therefrom simultaneously with discharge of the aliquot based upon said portion with delivery as two dilutions from said valve assembly to different exterior locations.

5. The valve assembly according to claim 3 and internal wash channel means formed within said valve assembly, said wash channel means having an inlet and an outlet for rinse liquid and being constructed and arranged for rinsing the internal facing surfaces of said valve disc elements at least once during the operating cycle of said valve assembly, said wash channel means comprising a pair of radially spaced circumferential concentric grooves formed along the inner and outer portions of the interior facing surfaces of at least one of said outer valve disc elements the inner groove being located adjacent the inner peripherial portion of an outer valve disc element and the outer groove being located adjacent the outer peripheral portion of said outer valve disc element, said inner groove being endless and the outer groove extending substantially the full circumferential extent of said respective faces, a radially linking groove formed in said face and joining the respective inner and outer grooves, a source of rinse liquid located exterior of said valve assembly, additional passageway means for establishing communication to said source of rinse liquid and defining said inlet and outlet and being capable of introducing rinse liquid to said washing channel means and discharging rinse liquid therefrom during the operating cycle of said valve assembly, rotation of said inner valve disc element effecting a sweep of said surface with flowing rinse liquid, the adjacent opposite face of said inner valve disc element having imperforate surface portions defining with said grooves said washing channel means when said elements are assembled and during rotation of said inner valve disc element, said inner valve disc element being rotatable substantially 360 degrees to effect a full rinse of said internal facing surfaces of said inner and outer valve disc elements.

6. The valve assembly according to claim 5 in which said grooves and said inlet and said outlet are formed in each stationary valve disc element and an additional internal through passageway is formed in said inner valve disc element to communicate with said washing channel means.

7. A method of providing plural dilutions of a single liquid sample comprising the steps of:
   establishing a continuous body of liquid sample from a source thereof and along a flow path within a single valve assembly;
   isolating plural aliquots of said liquid sample from said body within said flow path and within said valve assembly, said aliquots each having a precise volume and maintaining said aliquots distinct and isolated within said valve assembly;
   introducing liquid diluent into the said valve assembly and storing plural separated volumes of the liquid diluent within said valve assembly, said volumes being individually precise and maintaining said volumes individually isolated within said valve assembly;
   delivering one of the plural aliquots of said liquid sample and a selected one of said individual volumes of diluent to a first location exterior of said valve assembly for mixing thereat to form a first dilution of the liquid sample, while retaining stored the remaining aliquots of said liquid sample and the remaining individual volumes of diluent isolated within said valve assembly;
   introducing said first dilution into said valve assembly to establish therein a continuous body of said first dilution along a second flow path within said valve assembly independent of said first flow path;
   isolating an aliquot of said first dilution from said continuous body thereof along said second flow path within said valve assembly and maintaining said aliquot of the first dilution isolated; and
   delivering said aliquot of the first dilution and a selected one of the volumes of diluent to a predetermined exterior location while simultaneously delivering an isolated stored aliquot of the liquid sample along with a selected other one of the volumes of diluent to another exterior location, respectively.

8. The method as claimed in claim 7 and the steps of:
   establishing a third flow path within said valve assembly, the third flow path being independent of the first and second flow paths and including a portion formed along an area within said valve assembly;
   introducing rinse solution along said third flow path so that said portion is capable of sweeping the interior facing surfaces within said valve asesmbly; and
   sweeping said surfaces while flow along said last mentioned path continues.

9. The method as claimed in claims 7 or 8 in which all metering is performed within said valve assembly.

10. A method of providing a plurality of sample dilutions from a single liquid sample source, each dilution having a precise concentration; said method comprising the steps of: aspirating liquid sample from a source thereof forming a continuous body of liquid sample through a sampling valve consisting of a central rotatable valve disc element sandwiched between a pair of outer stationary valve disc elements and including three segmenting passageways of precise interior volume; rotating the rotatable valve disc element to isolate a pair of aliquots of the liquid sample within two of the segementing passageways; directing a precise volume of diluent to one of said pair of aliquots to drive said one aliquot and diluent to a location exterior of the sampling valve and mixing said one aliquot and diluent to form a first dilution while the other aliquot is retained; withdrawing the formed first dilution from said location and introducing said first dilution into the sampling valve forming a continuous body of said first dilution therethrough while maintaining the isolation of the other aliquot; rotating the central valve disc element to isolate an aliquot of said first dilution from the continuous body thereof and directing a precise volume of diluent to each remaining aliquot, driving each aliquot with said precise volume of diluent to different locations exterior of the valve assembly for the study of each dilution formed thereby.

11. A liquid sampling metering and transfer valve assembly of the type for use in diluting apparatus of the type employed in a particle study system, said valve assembly including a pair of spaced outer stationary valve disc elements and an inner rotatable valve disc element sandwiched therebetween, said inner valve disc element having opposite faces sealingly frictionally engaged with the adjacent faces of said outer elements, internal segmenting passageways formed in said inner rotatable valve disc element for metering, isolating and storing precise plural volumes of liquid sample therein as respective aliquot volumes thereof, plural loops integral with one of said outer valve disc elements for metering, isolating and storing precise volumes of liquid diluent therein as respective aliquot volumes thereof, the number of metered, isolated and stored volumes of liquid sample and liquid diluent being equal, each stored volume of liquid diluent being sufficient to form a dilution of precise concentration with a respective aliquot volume of liquid sample, said valve assembly capable of delivering each said dilution respectively to a location exterior of said valve assembly, plural first complementary counterpart passageways formed in one of said outer valve disc elements constructed and arranged for placement in communication with select ones of said internal segmentaing passageways sequentially upon step-wise rotation of said inner valve disc element for leading each aliquot into and out from the valve assembly and second complementary counterpart passageways formed in each of said inner and outer valve disc elements for leading diluent through said valve assembly following a path into and out from said internal segmenting passageways and said loops respectively whereby to form said dilutions, to load each loop with diluent and to deliver the respective dilutions to the appropriate locations.

12. The valve assembly according to claim 11 wherein the diluting apparatus includes a chamber exterior of said valve assembly and containing a predetermined volume of liquid diluent therein, one of said internal segmenting passageways is capable of placement in communication with said exterior chamber at a time subsequent to isolation of a liquid sample aliquot therein for delivery of said liquid sample aliquot thereto along with a selected one of the liquie diluent aliquots, another of said internal segmenting passageways and complementary counterpart passageways capable of receiving a portion of the mixture of said delivered liquid sample aliquot, said liquid diluent aliquot and predetermined volume of liquid diluent within the exterior chamber from the exterior chamber for metering, isolation and storage of an aliquot of said portion upon further rotation of said inner valve disc element, there being a still other internal segmenting passageway containing an original aliquot of liquid sample isolated and retained therein and dischargable therefrom simultaneously with discharge of said aliquot of said portion of respectively different selected locations exterior of said valve assembly.

* * * * *